United States Patent [19]

Murakami et al.

[11] Patent Number: 5,659,066

[45] Date of Patent: Aug. 19, 1997

[54] METHOD FOR CRYSTALLIZING α-L-ASPARTYL-L-PHENYLALANINE METHYL ESTER

[75] Inventors: Tsugio Murakami; Hidetaka Egashira; Kengo Okajima; Hidetoshi Wakamatsu, all of Yamaguchi, Japan

[73] Assignee: Holland Sweetner Company V.o.F., Maastricht, Netherlands

[21] Appl. No.: 618,602

[22] Filed: Mar. 20, 1996

[30] Foreign Application Priority Data

Mar. 20, 1995 [EP] European Pat. Off. ............ 95200659

[51] Int. Cl.$^6$ .................................................... C07K 5/06
[52] U.S. Cl. ............................................................ 560/41
[58] Field of Search ................................................ 560/41

[56] References Cited

U.S. PATENT DOCUMENTS 3,786,039  1/1974  Ariyoshi et al. ............................ 560/41
4,284,721  8/1981  Oyama et al. .......................... 435/68.1

FOREIGN PATENT DOCUMENTS 091 787   9/1985  European Pat. Off. .
533 222   3/1993  European Pat. Off. .
582 351   2/1994  European Pat. Off. .
2-243699  9/1990  Japan .

*Primary Examiner*—Johann Richter
*Assistant Examiner*—Laura L. Stockton
*Attorney, Agent, or Firm*—Cushman Darby & Cushman IP Group of Pillsbury Madison & Sutro, LLP

[57] ABSTRACT

Described herein is a method for crystallizing aspartame (APM) by cooling an aqueous solution containing APM without forced convection during part of the crystallization, wherein a clear aqueous APM solution is initially cooled under forced convection and forced convection is interrupted, after crystallization has started but before the concentration of the APM crystals formed in the system reaches 0.5% by weight, until the amount of crystals reaches at least 10%, but not more than 50%, of the target amount, and wherein cooling is interrupted for at least part of the time of said interruption of forced convection at about the same time or shortly thereafter.

15 Claims, No Drawings

METHOD FOR CRYSTALLIZING α-L-ASPARTYL-L-PHENYLALANINE METHYL ESTER

FIELD OF THE INVENTION

This invention relates to a method for crystallizing α-L-aspartyl-L-phenylalanine methyl ester (hereinafter also referred to as aspartame or "APM") by cooling an aqueous solution containing APM without forced convection during part of the crystallization. Aspartame finds wide application as a low-calorie sweetener because of its high-quality sweetness, aspartame being about 200 times as sweet as sugar.

PRIOR ART

APM can be synthesized by various methods. Industrial processes for producing APM include a process in which an N-protected L-aspartic acid is condensed with L-phenylalanine methyl ester in the presence of an enzyme, followed by the elimination of the protecting group U.S. Pat. No. 4,284,721, and a process in which an N-protected L-aspartic acid anhydride is coupled with L-phenylalanine methyl ester in an organic solvent and the protecting group is eliminated in accordance with conventional methods U.S. Pat. No. 3,786,039.

In any process, a crystallization step is indispensable to obtain the final product by isolation of APM from the reaction mixture. The crystallization step is usually carried out by (i) precipitating APM crystals through cooling of (a) an APM solution (in water, an organic solvent or a water-containing organic solvent) obtained via synthesis and purification steps or (b) an APM solution prepared by redissolving crude APM product into water, an organic solvent or a water-containing organic solvent, (ii) subjecting the precipitated crystals to solid-liquid separation and dewatering, e.g. by use of a centrifugal separator, and then (iii) drying the dewatered crystals to give the final product.

Hereinafter, unless explicitly defined otherwise, the general term "APM solution" is used to refer to an APM solution in water, an organic solution of APM or a solution of APM in a water-containing organic solvent; the term "aqueous solution" is used to refer to a solution in water (only).

According to the state of the art precipitation of APM crystals through cooling (cooling crystallization) is usually carried out by using (i) a crystallizer provided with a stirrer and a cooling/heat-transfer surface or (ii) a crystallizer provided with a heat-exchanger of external circulation type. In another known method crystallization is effected through conductive heat transfer without forced flow to improve the crystal properties of APM (EP-B-0.091.787).

In Ex.3 of JP-A-90-243699 (hereinafter also referred to as '699) it is incidentally shown that cooling crystallization without forced convection may be preceded by forced convection cooling if forced convection is stopped at the same time as crystallization starts. Thus, Ex.3 of '699 describes an experiment involving crystallization from an aqueous APM solution by cooling where stirring is stopped exactly at the time when crystallization starts and no stirring is applied for 45 minutes thereafter, with continuation of cooling.

When APM is crystallized through cooling in a crystallizer which utilizes forced flow, for example produced by ordinary mechanical stirring or external circulation, fine needle-like crystals are obtained, which are poor in solid-liquid separability and dewatering properties. Such crystals, moreover, readily adhere to the cooling/heat-transfer surface and thereby form so-called scale, which must be removed at regular intervals with interruption of the crystallizing operation since it impairs the efficiency of heat transfer. Moreover, since the crystals are fine and have a high water content, various problems arise during drying and further handling. In the drying step, for example, a product with an undesirably high impurity is obtained because of the large amount of mother liquor (containing impurities) which remains attached to the APM crystals. The dry product also contains many fine particles or may exhibit strong scattering in the form of fine powder.

In order to avoid such problems, the above-mentioned EP-B-0.091.787 ('787), which is considered to be the nearest state of the art for the present invention, proposes a crystallization method in which an APM solution, which may be an aqueous solution, is cooled through conductive heat transfer to form a pseudo-solid phase without forced flow produced by mechanical stirring or the like, followed by further cooling of the system, optionally with stirring, where required. In the method of cooling crystallization according to '787 static crystallization conditions should be maintained during at least the first 75% of crystallization, because otherwise poor quality crystals are obtained. Rather poor quality crystals are also obtained when using the method of Ex.3 of '699 and continuing the cooling process.

The '787 and '699 methods may indeed result in APM crystals having favourable filtering and dewatering properties. However, the efficiency of these methods is relatively poor since cooling (or a major part thereof) is effected through conductive heat transfer without forced flow. Such a method requires a large conductive surface area, and because a sherbet-like pseudo-solid phase is formed and stirring is not allowed until the last part of the crystallization, special equipment is needed, for instance such as shown in FIG. 9 of '787. For these reasons, the costs of, for example, the '787 method are high.

Moreover, especially in the '787 method, but also to a significant extent in the '699 method, the temperature of places nearer to the cooling surface is lower and the temperature of places further away from the cooling surface is higher. Accordingly, the solution or system as a whole is heterogeneous, and also its degree of supersaturation (which means the actual concentration of APM in the solution minus the solubility of APM under the prevailing conditions) is unevenly distributed over the contents of the crystallizer. Because of this, crystallization of APM starts at places where the temperature is lower, the supersaturation being higher at such places, and the system becomes even more heterogeneous. This necessarily leads to inhomogeneity in the crystalline products obtained.

OBJECT OF THE INVENTION

It is an object of this invention to provide a method of crystallizing APM by cooling an aqueous solution containing APM without forced convection during part of the crystallization to obtain big and relatively homogeneous APM crystals which exhibit good filtering and drying properties, and hence have production, handling (e.g. packing or transporting) and quality advantages.

Measures Taken to Solve the Problem

In view of the above, the inventors have conducted intensive investigations to solve the above problems in order to improve the industrial production of APM crystals and as a result have found, surprisingly, that APM crystals of an advantageous, large size can be obtained by cooling an aqueous solution containing APM without forced convection during part of the crystallization, this being achieved in that a clear aqueous solution containing APM is initially cooled under forced convection and forced convection is interrupted, after crystallization of α-L-aspartyl-L-phenylalanine methyl ester has started but before the concentration of the crystals formed in the system reaches 0.5% by weight, until the amount of crystals reaches at least 10%, but not more than 50%, of the target amount, and in that cooling is interrupted at about the same time or shortly after forced convection is interrupted, this interruption of cooling lasting for at least part of the time of said interruption of forced convection. This invention has been completed based on the above findings.

Accordingly, this invention provides a method for crystallizing α-L-aspartyl-L-phenylalanine methyl ester by cooling an aqueous solution containing α-L-aspartyl-L-phenylalanine methyl ester without forced convection during part of the crystallization, wherein a clear aqueous solution containing α-L-aspartyl-L-phenylalanine methyl ester is initially cooled under forced convection and forced convection is interrupted, after crystallization of α-L-aspartyl-L-phenylalanine methyl ester has started but before the concentration of the crystals formed in the system reaches 0.5% by weight, until the amount of crystals reaches at least 10%, but not more than 50%, of the target amount, and wherein cooling is interrupted at about the same time or shortly after forced convection is interrupted, this interruption of cooling lasting for at least part of the time of said interruption of forced convection.

Below, the invention will further be explained.

Clear aqueous APM solutions (that is solutions of APM in water) are cooled efficiently with forced convection. Such forced convection can be created e.g. by using an external circulation pump, or by mechanical stirring using various types of stirring blades, or by applying vacuum evaporation. Preferably, stirring blades are used. For the optimum cooling effect use is made of equipment with a cooling coil, cooling plates, a cooling jacket or an external circulation cooler.

Aqueous APM solutions suitable for use in this invention are clear solutions to begin with, and their temperature range is not limited as long as the temperature is (i) higher than the temperature at which precipitation of APM crystals starts, and (ii) lower than the temperature at which serious decomposition of APM would occur, e.g. by diketopiperazine formation.

In general, a temperature in the range of 50°–65° C. is preferable because a large amount of APM can be dissolved in the solution at such a temperature, whereas the amount of APM which decomposes into diketopiperazine is small.

The pH of the solution is preferably 3–6, more preferably 4–5, in order to minimize decomposition of APM; the APM concentration of the solution is preferably 2–6 wt % to obtain a large yield of APM crystals.

The cooling rate during forced convection cooling before forced convection is interrupted (further also referred to as "the initial cooling rate") is preferably 2° C./hr or more, so that decomposition of APM is reduced because of a shorter cooling time, and big APM crystals are obtained because the degree of supersaturation increases and APM crystals are growing at a higher rate. More preferably, this cooling rate is 5° C./hr or more, and 10° C./hr or more is even more preferable. However, if the cooling rate is very high, a huge cooling capacity is required and the costs of the cooling equipment increase. Therefore, in general an initial cooling rate of 50° C./hr or less is preferable.

According to the present invention forced convection is interrupted after precipitation of APM crystals has started but before the concentration of the crystals formed in the system reaches 0.5% by weight and cooling is interrupted at about the same time or shortly thereafter. Most preferably, cooling is interrupted before the temperature has dropped more than 3° C. after interruption of forced convection. The interval between interruption of forced convection and interruption of cooling therefore may be up to about 30 minutes.

It is repeated here that Example 3 of '699 describes an experiment involving crystallization from an aqueous APM solution by cooling where stirring is stopped exactly when crystallization starts and remains stopped for 45 minutes thereafter, with continuation of cooling. In the present method, the time from precipitation of the first APM crystals to interruption of forced convection and of cooling at about the same time or shortly thereafter is preferably short, but should not exceed the time necessary for precipitation of so many APM crystals that their concentration in the system reaches more than 0.5% by weight; more particularly, interruption of forced convection and of cooling at about the same time or shortly thereafter should start preferably when the concentration of crystals in the system reaches 0.01–0.4% by weight. When the time before the interruptions is too short, the total crystallization time becomes unnecessarily long, the APM crystals obtained are small in number and insufficient crystal growth takes place. If forced convection and cooling are interrupted before precipitation of APM crystals, the results are even worse. If the time before the interruptions is too long (i.e. when more than 0.5% by weight of crystals has formed in the system), the rate of nucleation is too fast so that too many APM crystals are obtained, and the APM crystals finally obtained have poor filtering properties because they are fine and short. The results therefore are found to be related to the degree of supersaturation, the rate of nucleation and the growth rate of APM crystals.

The detection of the start of precipitation of APM crystals can be carried out visually or by measuring the change of pH (viz., depending on the starting pH, the pH decreases or increases when APM crystals are precipitated); however, use of a turbidity meter to determine changes in light permeability is preferable because of this is an easier and more accurate method. The turbidity changes significantly when the precipitation of APM crystals starts.

Using a turbidity meter, the amount of APM crystals which is preferably present before the interruption of forced convection (and of cooling) can be easily estimated from the turbidity of the precipitation system, so that forced convection (and cooling) can be interrupted at the time the amount of initial APM crystals has reached the most preferable range. In the preferable range described above, nuclei of APM crystals are being generated at a proper rate, and uniform and relatively thick APM crystals are obtained, because initial APM crystals grow well after the interruption of forced convection; the APM crystals finally obtained have extremely good filtering properties.

After interruption of forced convection (and of cooling), the precipitation of APM crystals continues till depletion of supersaturation. According to the present invention, forced convection (and cooling) should not be restarted before the amount of crystals reaches at least 10% of the target amount, but there is no specific need to restart forced convection and cooling at the same time. Cooling may already be restarted shortly before forced convection is started again, but it is preferred to restart forced convection before cooling is restarted. The period of interruption of forced convection usually lasts 0.2 hours or more, preferably at least 0.5 hours, because a larger amount of APM crystals is obtained when the interruption is longer. On the other hand, the upper limit for this period is about 5 hours, because at longer interruption times no additional crystals are formed, and more preferably about 2 hours, because only few additional crystals are formed after 2 hours.

Applicant has found that a sherbet-like pseudo-solid phase as described in '787 is not formed during the interruption of forced convection. It is thought that such a difference may be caused by the complete absence of forced convection in the method of '787 until at least 75% of the possible crystals has precipitated.

Cooling of the APM solution may be stopped simultaneously with the interruption of forced convection or shortly thereafter, that is before the temperature has dropped more than 3° C. after interruption of forced convection. However, it is preferable to stop cooling for about the time of said interruption of forced convection in order to obtain the most homogeneous and largest APM crystals. If, as in Example 3 of '699, cooling is not stopped during the interruption of forced convection and the temperature of the APM solution is decreased, an uneven temperature distribution will result and thus also a heterogeneous degree of supersaturation because of the lack of forced convection. As a result, differences are caused in the nucleation rate and growth rate of the crystals, the homogeneity of the APM crystals obtained decreases and the number of relatively small crystals increases. If cooling is stopped (or the temperature is not decreased during such interruption), the temperature and degree of supersaturation remain more homogeneous. Therefore, differences in the nucleation rate and growth rate of the crystals are almost absent in the whole system, and big and uniform APM crystals having good filtering properties are obtained. In general, the temperature can be maintained by stopping cooling, and special operation and equipment are usually unnecessary, because the temperature becomes almost constant during the period when forced convection is stopped. Constant is here understood to mean that the temperature will not decrease by more than 3° C. Cooling water or cooling media may remain as they are in e.g. cooling jacket, cooling coil or cooling plates, without this resulting in any significant change in the temperature distribution, because the amounts of such cooling media are very small as compared to the total contents and material of the equipment itself. A temperature decrease of about 3° C. is not a problem for actual operation according to this preferred embodiment of the present invention. It is, however, preferred, in order to keep the temperature constant, to replace the circulating cooling medium by one having the same temperature as that of the total system when forced convection is interrupted.

Forced convection should be started again when the amount of crystals is at least 10% of the target amount. This amount of crystals is preferably 20% or more, more preferably 30% or more, and the upper limit is about 50% for overall efficiency considerations.

The target amount of APM crystals is the total amount or weight of APM crystals which can be precipitated from the crystallization system at the final, i.e. the lowest temperature of the system. This target amount can be estimated easily based on data on the solubility of APM at various temperatures; this amount primarily changes with the final temperature and, to a lesser extent, with the concentration of impurities. The exact solubility of APM in the actual system from which it is to be crystallized can be determined previously/separately by means of crystallization experiments involving samples of the starting solution.

In a further preferred embodiment of the invention APM slurry is withdrawn from the system as soon as forced convection is restarted, with simultaneous addition of equal amounts of fresh solution.

At about the time forced convection is restarted the APM solution (the crystallizing system) may be cooled further at a cooling rate which may be comparable to the initial cooling rate or lower. If a larger amount of APM crystals is to be obtained in a relatively short time, such further cooling of the APM system should be applied. Such optional further cooling should always be taken into consideration when determining "the target amount of crystals". In this case, relatively thick, precipitated APM crystals already grow as seed crystals and APM crystals having good filtering properties are obtained in a good yield. Final cooling to 5°–10° C. is preferable because of this increases the yield of crystals.

In this invention, there are almost no problems of scaling, and even if some scaling does occur, the scale can be removed easily by the forced convection used.

In the present invention, the pH of the starting APM solution is not limited, but a pH of 3–6 is preferable, and a pH of 4–5 is especially desirable because the amount and the growth rate of precipitated APM crystals increase.

The solid-liquid separation of the slurry of APM crystals obtained, either after finishing of the batchwise crystallization of the APM solution and—if necessary—converting the crystallization system obtained into an easily movable slurry, or, as in the preferred mode of continuous withdrawal of a slurry of crystals after forced convection is restarted, with simultaneous addition of equal amounts of fresh solution, can be effected either by batchwise operation or by continuous operation, and a high degree of dehydration can be achieved in a short time.

As mentioned above, in a preferred embodiment of the present invention the slurry obtained during the crystallization process is continuously withdrawn from the system as soon as forced convection is restarted. Crystallization is then continued continuously, while fresh APM solution is fed to the system in an amount roughly corresponding to the amount of slurry withdrawn for the solid-liquid separation in this continuous embodiment. The mother liquor of the solid-liquid separation step can also be returned to the crystallizer, or it can be cooled further to increase the amount of APM crystals obtained.

As solid-liquid separators, use can be made of any type of centrifuge or filtration equipment, such as filter press, belt filter and drum filter, conventionally used in industrial operations. If necessary, the crystal cake obtained may be washed by water or APM solution; preferably the water or the APM solution used is cold, for instance 5°–10° C., so that redissolving of APM is minimized. Washing is easy and improves the quality of APM crystals because the mother liquid attached to the APM crystals is removed. The wet cake obtained may be dried after granulation or as it is. As dryers, stream dryers, fluidized bed dryers, drum dryers, and high speed rotating paddle dryers can be used. Drying may also be effected at reduced pressure.

In this method, the average particle size of APM crystals becomes extremely large, and the particles are very uniform and homogeneous. The APM crystals obtained are crystals that have grown well in the direction of their short axis. The reason for this is not completely understood, but it appears that nucleation of APM crystals takes place in a homogeneous and proper manner when forced convection is applied because of the homogeneous temperature and the homogeneous degree of supersaturation. Therefore, it seems that homogeneous and large APM crystals having good filtering properties are obtained because of the high growth rate, especially in the direction of the short axis.

Effects of this Invention

In this invention, the cooling efficiency is extremely high because cooling is carried out during the major part, or almost the complete period, of crystallization under forced convection, and crystallizer(s) and cooling equipment can be manufactured compactly because special equipment is not necessary. Moreover, the method of this invention is economically very advantageous because cooling times are short and the cooling energy requirements low. APM solutions are homogeneous during the time they are cooled under forced convection, and crystallization of APM is carried out without any significant temperature gradient. As a result, precipitation of APM occurs throughout the entire system, and the APM crystals grow homogeneously. Therefore, uniform and large APM crystals having good filtering properties are obtained. The effects obtained by the method of this invention are summarized as follows:

(1) Crystallization can be carried out in a single process, and equipment can be manufactured compactly. Moreover, the equipment can be operated easily, and the energy requirements of the process are very low. Therefore, this invention can be applied in and is useful for large volume production of APM on an industrial scale.

(2) APM crystals obtained by this crystallization method are large and uniform; and APM wet cakes which have a small amount of water attached to the crystals and have a low amount of impurities are obtained during short time periods because filtering and washing of the APM crystals is extremely easy.

(3) Drying of the APM cakes is easy because the amount of water attached to the crystals is low, and the cakes can be dried during a short period of time at a moderate temperature using only little drying energy in order to obtain APM crystals. Moreover, no deterioration of products is observed during such drying, and APM having a high quality can be obtained.

Furthermore, the amount of fine powder formed in the drying process is very small, and this is very useful for actual operation.

(4) Scattering of the dried products occurs only to a very limited extent, and this is extremely advantageous in handling the final products.

(5) If desired, the quality of APM crystals precipitated using conventional methods of crystallization can be improved by means of addition (as seed crystals) of APM crystals obtained by the method of this invention and pulverized by wet grinding.

As mentioned above, this invention has many advantages in terms of actual operation, economical aspects, quality and handling of the product obtained.

EXAMPLES

This invention will hereinafter be explained by means of examples and comparative experiments. It should however be noted that this invention is by no means limited to these examples.

In the following examples and comparative experiments, the filtering rate of APM crystals was measured in the following manner: 500 ml of slurry containing precipitated APM crystals obtained in each example or experiment was sampled and filtered using a suction filter (double-walled glass flask, equipped with stirrer; leaf tester) fitted with a polypropylene cloth filter having an air permeability of 5 ml/cm²sec (12 mm $H_2O$; 117 Pa); each slurry was filtered at a differential pressure of $-400$ mm Hg (53.3 kPa), the slurry being poured carefully onto the filter so that filtering could be performed continuously without drying up of the slurry on the filter cloth. The filtering rate was calculated from the period of time lapsed from the start to the completion of filtering (filtering was considered to be complete when liquid could no longer be seen above the filter cloth) and the volume of filtrate at the time of completion.

Example I 2 liters of aqueous 3.5 wt % APM solution of 60° C. were charged into a 2.5-liter glass flask equipped with external cooling jacket and stirrer, and then the pH of the solution was adjusted to 4.5 by addition of 1N aqueous NaOH. Then, the solution was cooled by circulating cooling water through the external cooling jacket at a cooling rate of 15° C./hour while stirring the solution at 300 rpm. Stirring and cooling were interrupted immediately when it was observed that APM crystals started precipitating (which occurred at 42.5° C.); the concentration of APM precipitated at that time was found to be 0.08% by weight. After one hour stirring and cooling were restarted (at which time about 26% of the target amount of APM crystals had crystallized) and the system was cooled to 10° C. No pseudo-solid phase ("sherbet") as described in '787 did form in the system. Crystal growth was good and no scaling was observed after discharge of the slurry finally obtained. Table 1 presents information on the crystal form and filtering rate of the APM crystals obtained in this Example.

Example II

This Example was carried out in the same manner as Example I, except that stirring and cooling were interrupted for 2 hours. Also in this Example stirring and cooling were interrupted immediately when it was observed that APM crystals started precipitating (at 42.5° C.); the concentration of APM precipitated at that time was found to be 0.08% by weight. Other observations were similar to those of Example I (with about 28% of final crystals being obtained before restarting stirring and cooling). Again, the growth of APM crystals was good, and no scaling problems were observed. Table 1 presents information on the crystal form and filtering rate of the APM crystals obtained.

Example III

This Example was carried out in the same manner as Example I, except that only stirring was interrupted immediately when it was observed that APM crystals started precipitating (at 43.0° C.); somewhat later, when the temperature had decreased to 41.0° C., cooling was interrupted and stirring and cooling were restarted 1 hour after stirring had been interrupted. The concentration of APM precipitated directly after interruption of stirring was found to be 0.05% by weight, and good growth of APM crystals was observed. The temperature in the system after restarting of stirring was found to be 40° C. Almost no scaling was observed at the end of the experiment. The results are shown in Table 1.

Example IV

This example was carried out in the same manner as Example I, except that the start of precipitation of APM was determined by measuring the light permeability using a turbidity meter (recording titrator, manufactured by Hiranuma Industry Co. Ltd., type: COMITITE-101) instead of by visual detection. Stirring and cooling were interrupted immediately when the transmissivity of light changed by 100 mV. The detection of precipitaton of APM crystals was extremely easy, and the concentration of APM precipitated first was found to be 0.05% by weight at the time stirring and cooling were interrupted. No scaling was observed after discharge of the slurry finally obtained. The results are shown in Table 1.

Comparative Experiment A

This Comparative Experiment was carried out in the same way as Example I, except that crystallization of APM was carried out without interruption of stirring and cooling. The crystals obtained were fine and needle-like, and considerable scaling had occurred. Table 1 presents information on the crystal form and filtering rate of APM crystals obtained.

Comparative Experiment B

This Comparative Experiment was carried out in the same way as Example I, except that both stirring and cooling were continued after visual detection of the start of precipitation of APM crystals (42.5° C.), while stirring and cooling were interrupted immediately when the temperature of the system became 40° C. At that time, the concentration of APM precipitated was found to be 1.0% by weight; almost all APM crystals were fine and needle-like, and much scaling had occurred. Stirring and cooling were restarted after 1 hour, and then the APM slurry was cooled further to 10° C. Despite stirring, a substantial part of the scale could not be removed. Table 1 presents information on the crystal form and filtering rate of the APM crystals obtained.

Comparative Experiment C

This Comparative Experiment was carried out in the same way as Example I, except that stirring and cooling were interrupted at 44° C. before the start of precipitation of APM crystals could be determined visually. Quite some scaling was observed, and the amount of APM crystals precipitated during the interruption of stirring was extremely small, while the APM crystals which precipitated after restarting of stirring and cooling were fine and needle-like. Part of the scale could not be removed. Table 1 presents information on the crystal form and filtering rate of the APM crystals obtained.

Comparative Example D

This Comparative Example, being similar to Example 3 of '699, was carried out in the same manner as Example I, except that cooling was not interrupted at all. Stirring was interrupted immediately when it was observed that APM crystals started precipitating (at 43.0° C.); the concentration of APM precipitated at that time was determined to be 0.08% by weight. Cooling was continued without interruption. The cooling efficiency, however, was considerably lowered, and quite some scaling occurred. Stirring was restarted when the temperature became 36.5° C. (after stirring had been interrupted for about 1 hour), and cooling was continued to 10° C. Despite the stirring, a substantial part of the scale could not be removed. As can be seen from Table 1, the crystal length was shorter than according to the method of the invention, though the filtering rate of the APM crystals obtained was at about the same level. The particle size distribution of the crystals obtained appeared to be somewhat wider than in the Examples.

In all the above Examples, except for the Comparative Experiments, it thus turned out to be possible to obtain big and homogeneous APM crystals of relatively uniform particle size. In further processing these crystals exhibited good filtering and drying properties, and hence they have production, handling (e.g. packing or transporting) and quality advantages.

TABLE 1

| Example/ Comp. Exp. | Amount originally precipitated (%)[2] | Form of APM crystals and dimensions[1] | Filtering rate ($l/m^2 \cdot min.$) |
| --- | --- | --- | --- |
| I | 26 | Pillar-shaped 5–20 × 100 or more | 287 |
| II | 28 | idem | 305 |
| III | 37 | idem | 300 |
| IV | 30 | Pillar-shaped 5–20 × 100 or more | 291 |
| Comp. A | — | Needle-like 10 or less × 50–100 | 88 |
| Comp. B | 55 | Needle-like 10 or less × 50–100 | 118 |
| Comp. C | 8 | Needle-like 20 or less × 50 or more | 149 |
| Comp. D | 48 | Needle-like and pillar-shaped 1–20 × 50 or more | 272 |

[1] Dimensions are indicated in [length of short axis] times [length of long axis], both in µm
[2] Amount of APM precipitated at the time forced convection is started again, calculated as percentage of the target amount of APM crystals

We claim:

1. A method for crystallizing α-L-aspartyl-L-phenylalanine methyl ester by cooling an aqueous solution containing α-L-aspartyl-L-phenylalanine methyl ester without forced convection during part of the crystallization, wherein a clear aqueous solution containing α-L-aspartyl-L-phenylalanine methyl ester is initially cooled under forced convection and forced convection is interrupted, after crystallization of α-L-aspartyl-L-phenylalanine methyl ester has started but before the concentration of the crystals formed in the system reaches 0.5% by weight, until the amount of crystals reaches at least 10%, but not more than 50%, of the target amount, and wherein cooling is interrupted at about the same time or shortly after forced convection is interrupted, this interruption of cooling lasting for at least part of the time of said interruption of forced convection.

2. A method for crystallizing α-L-aspartyl-L-phenylalanine methyl ester according to claim 1, wherein the interruption of the forced convection is started when the concentration of crystals formed in the system reaches 0.01–0.4% by weight.

3. A method for crystallizing α-L-aspartyl-L-phenylalanine methyl ester according to either of claims 1 or 2, wherein the concentration of α-L-aspartyl-L-phenylalanine methyl ester in the solution is 2 to 6% by weight.

4. A method for crystallizing α-L-aspartyl-L-phenylalanine methyl ester according to any of claims 1 or 2, wherein the temperature of said solution is not decreased by more than 3° C. for at least about the period forced convection is interrupted.

5. A method for crystallizing α-L-aspartyl-L-phenylalanine methyl ester according to any of claims 1 or 2, wherein the cooling is interrupted for at least about the period forced convection is interrupted.

6. A method for crystallizing α-L-aspartyl-L-phenylalanine methyl ester according to any of claims 1 or 2, wherein α-L-aspartyl-L-phenylalanine methyl ester slurry is withdrawn continuously from the system as soon as forced convection is restarted with simultaneous addition of equal amounts of fresh solution.

7. A method for crystallizing α-L-aspartyl-L-phenylalanine methyl ester according to claim 5, wherein cooling is restarted at about the time when forced convection is restarted.

8. A method for crystallizing α-L-aspartyl-L-phenylalanine methyl ester according to any of claims 1 or 2, wherein cooling is carried out until a temperature in the range of 5°–10° C. is reached.

9. A method for crystallizing α-L-aspartyl-L-phenylalanine methyl ester according to any of claims 1 or 2, wherein the initial cooling rate is between 2° C./hour and 50° C./hour.

10. A method for crystallizing α-L-aspartyl-L-phenylalanine methyl ester according to any of claims 1 or 2, wherein detection of the start of crystallization is carried out using a turbidity meter.

11. A method for crystallizing α-L-aspartyl-L-phenylalanine methyl ester according to any of claims 1 or 2, wherein forced convection is restarted when the amount of α-L-aspartyl-L-phenylalanine methyl ester crystals obtained is at least 20% but less than 50% of the target amount.

12. A method for crystallizing α-L-aspartyl-L-phenylalanine methyl ester according to any of claims 1 or 2, wherein the pH of the α-L-aspartyl-L-phenylalanine methyl ester solution is in the range of 3–6.

13. A method for crystallizing α-L-aspartyl-L-phenylalanine methyl ester according to claim 6, wherein cooling is restarted at about the time when forced convection is restarted.

14. A method for crystallizing α-L-aspartyl-L-phenylalanine methyl ester according to claim 1 or 2, wherein the pH of the α-L-aspartyl-L-phenylalanine methyl ester solution is in the range of 4–5.

15. A method for crystallizing α-L-aspartyl-L-phenylalanine methyl ester according to claim 2, wherein the temperature of said solution is not decreased by more than 3° C. for at least about the period forced convection is interrupted.

* * * * *